United States Patent [19]

Yasuda et al.

[11] 4,217,450
[45] Aug. 12, 1980

[54] IMIDAZOLEDICARBOXYLIC ACID SUBSTITUTED CEPHALOSPORIN DERIVATIVES

[75] Inventors: Naohiko Yasuda, Yokosuka; Chikahiko Eguchi; Masaru Okutsu, both of Kawaski; Yoshiteru Hirose, Kamakura, all of Japan

[73] Assignee: Ajinomoto Company, Incorporated, Tokyo, Japan

[21] Appl. No.: 913,369

[22] Filed: Jun. 7, 1978

[30] Foreign Application Priority Data

Jun. 16, 1977 [JP] Japan ................................ 52-71468

[51] Int. Cl.$^2$ ................. C07D 501/36; C07D 501/34; C07D 501/56
[52] U.S. Cl. ....................................... 544/25; 544/27; 544/28; 544/22; 260/239.1
[58] Field of Search ....................... 544/25, 27, 28, 22

[56] References Cited

U.S. PATENT DOCUMENTS 4,101,661 7/1978 Kaltenbroun et al. ................. 544/27
4,156,724 5/1979 Yamada et al. ......................... 544/27

Primary Examiner—Donald G. Daus
Assistant Examiner—David E. Wheeler
Attorney, Agent, or Firm—Oblon, Fisher, Spivak, McClelland & Maier

[57] ABSTRACT

Compounds having the following formula:

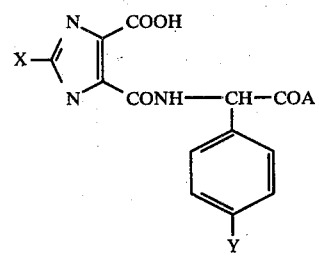

wherein X is a radical selected from the group consisting of hydrogen, halogen, hydroxy, mercapto, methyl and amino.

Y is a radical selected from the group consisting of hydrogen and hydroxy, and

A is an organic compound residue selected from the group consisting of having the formula:

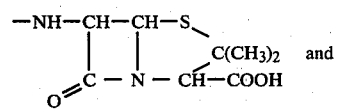

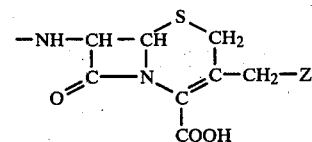

wherein Z is a radical selected from the group consisting hydrogen, acyloxy, carbamoyloxy, (heteroaromatic) thio, pyridinium, quinolinium and picolinium; and salts thereof, are useful as anti-bacterial agents active against *Pseudomonas aeruginosa*.

7 Claims, No Drawings

IMIDAZOLEDICARBOXYLIC ACID SUBSTITUTED CEPHALOSPORIN DERIVATIVES

BACKGROUND OF THE INVENTION

The present invention relates to novel imidazoledicarboxylic acid derivatives, which are useful as antibiotics, particularly as antibacterial agents in the treatment of infectious diseases caused by Pseudomonas aeruginosa in both human beings and other animals and intermediates therefor.

SUMMARY OF THE INVENTION

The present inventors have succeeded in synthesizing novel imidazoledicarboxylic acid derivatives, having the following formula:

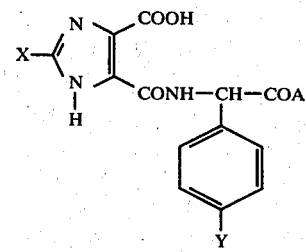

wherein X is a radical selected from the group consisting of hydrogen, halogen, hydroxy, mercapto group, methyl and amino, Y is a radical selected from the group consisting of hydrogen and hydroxy, and A is a organic compound residue having one of the following formulas:

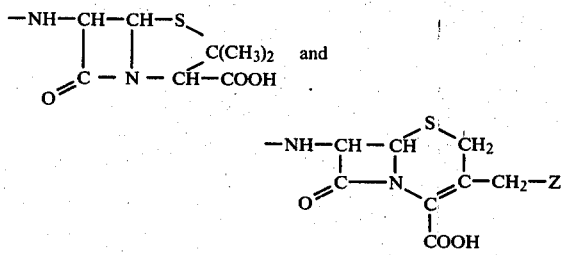

wherein Z is a radical selected from the group consisting of hydrogen, acyloxy, carbamoyloxy, (heteroaromatic)thio such as 5-(1-methyltetrazolyl)thio and 2-(1,3,4-thiadiazolyl)-thio, pyridinium such as 4-carbamoylpyridinium and 4-β-sulfoethylpyridinium, quinolinium and picolinium, and pharmaceutically acceptable nontoxic salts thereof, and have discovered that these novel compounds have a marked antibacterial activity, particularly against Pseudomonas aeruginosa and therefore can be used as antibiotics, or intermediate for antibiotics.

DESCRIPTION OF THE PREFERRED EMBODIMENTS

Amino acids which form the compounds of the present invention are phenylglycine and 4-hydroxyphenylglycine, which may be in the L-, D- and DL-form. In many cases, the D-form is suitable in view of its antibacterial activity.

Suitable pharmaceutically acceptable salts of such compounds are conventional non-toxic salts and may include metal salts such as an alkali metal salt (e.g., sodium salt, potassium salt, etc.) or an alkaline earth metal salt (e.g., calcium salt, magnesium salts, etc.), ammonium salts, organic amine salts (e.g., trimethylamine salt, triethylamine salt, pyridine salt, picoline salt, dicyclohexylamine salt, N,N'-dibenzylethylenediamine salt, procain salt, dibenzylammonium salt, N-benzyl-β-phenethylammonium salt etc.) and the like.

Such salts of the present inventiion are prepared by conventional methods, for example by neutralizing the free base form of a compound of the present invention with alkali.

It has been known that Penicillins and Cephalosporins having the following formula:

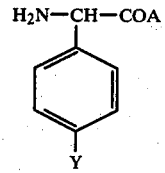

wherein Y and A have the same meanings as mentioned above, show antibacterial activity against not only gram positive bacteria but also gram negative bacteria. However, they show essentially no antibacterial activity against Pseudomonas aeruginosa which causes serious infectious diseases.

The imidazoledicarboxylic acid derivatives of the present invention have effective antibacterial activity against not only gram positive and gram negative bacteria but also Pseudomonas aeruginosa, and therefore have very broad-spectrum antibacterial activity.

The imidazoledicarboxylic acid derivatives of the present invention can be prepared by reacting a compound having the formula:

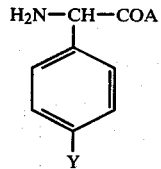

with a compound having the formula:

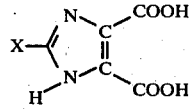

or its reactive carboxy group derivative, wherein X, Y and A have the same meanings as above, by a condensation reaction.

A suitable reactive derivative is the acid halide derivative.

For example, the acid chloride derivative is prepared by reacting a compound having the formula:

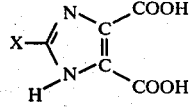

wherein X has the same meaning as above, with thionyl chloride or phosphorus pentachloride.

The present invention is explained precisely in the following Examples. In the Examples, the developing solvent for the thin-layer chromatography was a mixture of n-butanol, acetic acid and water in 6:3:2 volume ratio.

Example 1

Thionyl chloride (80 ml) was added to a mixture of imidazole-4,5-dicarboxylic acid (23.4 g, 150 mM), dry benzene 150 ml and dimethylformamide (DMF) (3 ml), and the thus obtained mixture was stirred at 85° C. for 5.5 hours under reflux. The mixture was concentrated to yield solid material under reduced pressure. The thus obtained material was suspended in dry benzene (100 ml) and then the mixture was concentrated to yield solid material under reduced pressure, once more. The thus obtained solid material, the acid chloride derivative

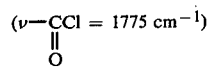

was suspended in dry dichloromethane (300 ml).

Anhydrous D,(−)-α-aminobenzylpenicillin (30.0 g, 75 mM) was suspended in dichloromethane (300 ml) and to the mixture triethylamine (100 ml) was added and then a homogeneous solution was prepared. The thus obtained D-(−)-α-aminobenzylpenicillin dichloromethane solution was added dropwise over 30 minutes little by little to the acid chloride derivative dichloromethane suspension prepared above with stirring in an ice bath. After addition of the D-(−)-α-aminobenzylpenicillin solution, the mixture was stirred for 2 hours in the ice bath. Insoluble material was removed by filtration and then the solution was concentrated at less than 30° C. under reduced pressure to yield solid material. The thus obtained solid material was dissolved in water (400 ml) and then to the mixture ethyl acetate (400 ml) was added to form two phases. The ethyl acetate layer was separated and removed. To the separated water layer ethyl acetate (500 ml) was added. To the mixture 6% HCl was added and thereby the water layer was adjusted to pH 2. The precipitated material was removed by filtration and a solution having two phases was obtained. The aqueous phase was separated and extracted with ethyl acetate (500 ml), once more. The ethyl acetate solutions were combined and dried with anhydrous magnesium sulfate. The ethyl acetate solution was concentrated at less than 40° C. to yield solid material. The thus obtained solid material was suspended in ethyl acetate (200 ml) and the mixture was stirred for 30 minutes at 60° C. An insoluble solid material was obtained by filtration and this material was dissolved in a mixture (80 ml) of methanol and ethyl acetate (1:1 by weight) by heating. Crystallization was carried out by adding ether to the solution obtained above. Crystallized solid material was obtained by filtration. Further crystallization was carried out by adding ether to the concentrated mother liquor. The solid materials obtained above were combined and thereby D-α-(4-carboxyimidazole-5-carboxyamido)benzylpenicillin (4.3 g, yield: 11.8%) was obtained.
M.P., 195°–204° C. (dec.)
Elemental analysis:
 Found C 50.77%, H 4.51%, N 14.00%, S 6.35%
 Calcd. for $C_{21}H_{21}N_5O_7S$

C 51.73%, H 4.35%, N 14.37%, S 6.58%

Thin Layer Chromatography (TLC) (silica gel) $R_f$=0.45 I.R. spectrum (Nujol)

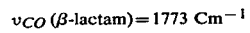

The thus obtained compound was converted to the disodium salt thereof by the following methods.

D-α-(4-carboxyimidazole-5-carboxyamido)benzylpenicillin (0.5 g, 1.0 mM) was dissolved in a mixture of methanol (15 ml) and ethyl acetate (10 ml) and to the solution thus obtained 2-ethylhexanecarboxylic acid sodium salt n-butanol solution (2 M/l) (1.23 ml) was added. The mixture was stirred for 10 minutes. Crystallized material was produced by adding ethyl acetate (150 ml) dropwise to the solution. Crystals were obtained by filtration and dried, and thereby D-α-(4-carboxyimidazole-5-carboxyamido)benzylpenicillin disodium salt monohydrate [I] (0.35 g) was obtained.
Elemental analysis:
 Found C 46.67%, H 4.19%, N 12.32%
 Calcd. for $C_{21}H_{19}N_5O_7SNa_2.1H_2O$
 C 45.90%, H 3.86%, N 12.74%
N.M.R. spectrum (D$_2$O, δ)
ppm 1.50 (b.s. 6H)

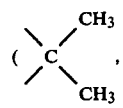

2nd position)
4.30 (s, 1H) (—H, 3rd position)
5.40–5.80 (m. 3H)

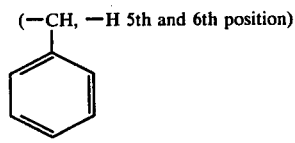

7.47 (b.s. 5H)

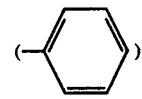

7.82 (s, 1H) (—H, 2nd position in imidazole)

Example 2

Imidazole-4,5-dicarboxylic acid (3.12 g, 20 mM) was suspended in dry benzene (40 ml) containing DMF (6 drops). To this mixture thionyl chloride (8 ml) was added. The mixture was reacted in the same manner as in Example 1 and the acid chloride derivative produced thereby was suspended in dry dichloromethane (40 ml).

Anhydrous 7-β-[D-(−)-α-aminophenylacetomido]cephalosporanic acid 4.05 g, 10 mM) was suspended in dichloromethane (40 ml). To this mixture triethyl amine (14 ml) was added and thereby a homogeneous solution was prepared.

7-β-[D-(−)-α-aminophenylacetoamido]cephalosporanic acid dichloromethane solution was added stepwise little by little to the acid chloride derivative dichloromethane suspension prepared above in an ice bath while stirring over a period of 15 minutes. After addition of the 7β-[D(-0-α-aminophenylacetoamide]-cephalosporanic acid, the mixture was further stirred for two hours in the ice bath. Insoluble material was removed by filtration, and the solution was concentrated at less than 30° C. under reduced pressure to yield solid material. The thus obtained solid material was dissolved in water (70 ml). To this mixture ethyl acetate (70 ml) was added and thereby a solution having two layers was prepared. The water solution was separated and to this solution ethyl acetate (100 ml) was added. 6% Hydrochloric acid was added to the mixture while stirring and thereby the water phase of the solution was adjusted to pH2. The precipitate was removed by filtration and a solution having two layers was obtained. The water solution was separated and extracted with ethyl acetate (100 ml), once more. The ethyl acetate solutions obtained were combined and dried with anhydrous magnesium sulphate. The ethyl acetate solution was concentrated at less than 30° C. and the solid material thus obtained was triturated by adding ether (100 ml) thereto, and separated by filtration. The powdered material was dried to give 7-β-[D-(-0-α-(4-carboxyimidazole-5-carboxyamido)phenylacetoamido]cephalosporanic acid monohydrate (1.87 g, yield: 34.4%).

M.P., 209°-218° C. (dec.)

Elemental analysis:
Found C 49.66%, H 3.98%, N 12.77%, S 5.66%
Calcd. for $C_{23}H_{21}N_5O_9S \cdot 1H_2O$
C 49.19%, H 4.14%, N 12.47%, S 5.71%

TLC (silica gel) $R_f = 0.70$
I.R. spectrum (Nujol)
$\nu CO(\beta\text{-lactam}) = 1775$ cm$^{-1}$
$\nu CO(-OCOCH_3) = 1745$ cm$^{-1}$ The compound thus obtained was converted to the disodium salt thereof in the same manner as in Example 1.

The N.M.R. spectrum of the disodium salt thus obtained is as follows: ($D_2O$, δ) ppm 2.13 (s, 3H) (—OCOCH$_3$)
3.36 (m, 2H) (<CH$_2$, 2nd position)
5.02 (d, 1H) (—H, 6th position)
5.73 (m, 2H) (—H, 7th position,

—CH—)

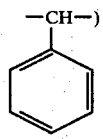

7.50 (bs, 5H)

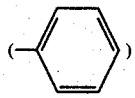

7.80 (s, H) (—H, 2nd position of imidazole)

Example 3

7-β-[D-(-)-α-(4-carboxyimidazole-5-carboxyamido)phenylacetoamido]cephalosporanic acid.2Na salt (587 mg, 1 mM) as produced in Example 2, was dissolved in water (5.6 ml). To this mixture isonicotinamide (244 mg, 2 mM) and potassium iodide (8.3 g) were added and this mixture was reacted with stirring at 70° C. for 2 hours. The reaction mixture was treated with Amberlite XAD-2 produced by Rohm & Haas Co. (450 ml) in a column. First, isonicotinamide was eluted with water. Next, the cephalosporin fraction which was eluted with a mixture of water and methanol (1:1) was collected. In the water-methanol solution thus obtained, methanol was removed and thereupon resultant water solution was lyophilized to give the desired compound, 7-β-[D-(-)-α-(4-carboxyimidazole-5-carbox-amido)-phenylacetoamido]-3-(4-carbamoylpyridinium)methyl-3-cephem-4-carboxylic acid.mixture of K and Na salt.-trihydrate [II] (90 mg, yield: 13%).

M.P., 185°-189° C. (dec.)

Elemental analysis:
Found C 47.27%, H 3.83%, N 13.79% S 4.75%, K 3.58%, Na 0.58%
Calcd. for $C_{27}H_{22}N_7O_8S \cdot K_{0.78}Na_{0.22} \cdot 3H_2O$ C 46.71%, H 4.07%, N 14.13% S 4.62%, K 4.39%, Na 0.73%

TLC (silica gel) $R_f = 0.71$
I.R. spectrum (Nujol):

$\nu_{C=O}(\beta\text{-lactam}) = 1770$ cm$^{-1}$

Example 4

2-Hydroxyimidazole-4,5-dicarboxylic acid (1 g, 6 mM) was suspended in dry benzene (15 ml) and to this mixture DMF (3 drops) and then thionyl chloride (2.5 ml) were added. The mixture was refluxed at 80° C. with stirring for 4.5 hours. The solution was concentrated under reduced pressure to yield solid material. The residue obtained was suspended in dry benzene (10 ml) and the solution was concentrated under reduced pressure to yield solid material, once more. The obtained acid chloride derivative

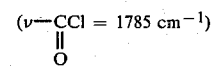

was suspended in dry dichlormethane (15 ml).

On the other hand, anhydrous D-(-)-α-aminobenzylpenicillin (1.05 g, 3 mM) was suspended in dry dichloromethane (10 ml) and to this mixture triethylamine (4.2 ml) was added to give a homogeneous solution.

D-(-)-α-aminobenzylpenicillin dichloromethane solution was added dropwise over 15 minutes to the acid chloride derivative dichloromethane suspension produced above with stirring and cooling. The thus obtained mixture was further stirred for two hours with cooling. Insoluble material was removed by filtration and the obtained filtrate was concentrated under reduced pressure at less than 30° C. to yield solid material. The thus obtained resulting solid material was dissolved in water (50 ml) and ethyl acetate (70 ml) was added thereto to give a solution having two layers. The ethyl acetate layer was separated and removed. Ethyl acetate (70 ml) was added to the water solution and 6% hydrochloric acid solution was added thereto with stirring to adjust the water solution thereof to pH2. The precipitate was removed by filtration and thereby a solution having two layers was obtained. The water solution was separated and extracted with ethyl acetate (70 ml), once more. The ethyl acetate solutions were combined and dried with anhydrous magnesium sulfate. The ethyl acetate solution was concentrated at less than 30° C. to yield solid material. The solid material was triturated with ether (30 ml) and separated by filtration. The solid material was dried to give the object compound, D-α-(2-hydroxy-4-carboxyimidazole-5-carboxamido)benzylpenicillin (0.37 g, yield 24.8%).
M.P., 230°–240° C. (dec.)
Elemental analysis:
  Found C 49.26%, H 4.10%, N 13.93% S 5.86%
  Calcd. for $C_{21}H_{21}N_5O_8S$ C 50.09%, H 4.21%, N 13.91% S 6.37%
TLC (silica gel) $R_f=0.58$
I.R. spectrum (Nujol)

$\nu_{C=O}(\beta\text{-lactam})=1770 \text{ cm}^{-1}$

The N.M.R. spectrum of the 2Na salt of this compound is as follows: ($D_2O$, δ)
ppm
  1.46 (bs, 6H)

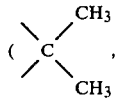

2nd position)
4.23 (s, 1H) (—H, 3rd position)
5.40–5.80 (m, 3H)

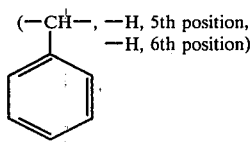

(—CH—, —H, 5th position,
—H, 6th position)

7.46 (bs, 5H)

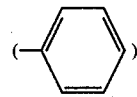

The disodium salt of this compound [III] was produced in the same manner as in Example 1.

Example 5

2-Mercaptoimidazole-4,5-dicarboxylic acid (1.88 g, 10 mM) was converted to the acid chloride derivative thereof

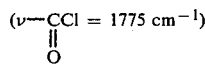
($\nu$—CCl = 1775 cm$^{-1}$)

in the same manner as in Example 4 and then this derivative was reacted with anhydrous D-(−)-α-aminobenzylpenicillin (1.75 g, 5 mM) to give D-α-(2-mercapto-4-carboxyimidazole-5-carboxamido)benzylpenicillin monohydrate (1.36 g, yield: 50.7%) in the same manner.
M.P., 178°–184° C. (dec.)
Elemental analysis:
  Found C 47.26%, H 4.14%, N 12.63%
  Calcd. for $C_{21}H_{21}N_5S_2O_7 \cdot H_2O$ C 46.91%, H 4.32%, N 13.03%
TLC (silica gel) $R_f=0.44$
I.R. spectrum (Nujol):

$\nu_{C=O}(\beta\text{-lactam})=1785 \text{ cm}^{-1}$

The N.M.R. spectrum of the 2Na salt of this compound is as follows: ($D_2O$, δ)
ppm
  1.48 (bs, 6H)

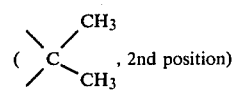
, 2nd position)

4.26 (s, 1H) (—H, 3rd position)
5.40–5.85 (m, 3H)

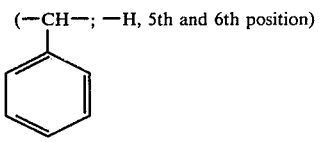
(—CH—; —H, 5th and 6th position)

7.40 (bs, 5H)

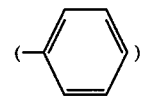

The disodium salt of this compound [IV] was produced in the same manner as in Example 1.

Example 6

2-Methylimidazole-4,5-dicarboxylic acid (1.7 g, 10 mM) was converted to the acid chloride derivative thereof

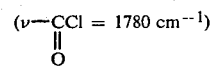
($\nu$—CCl = 1780 cm$^{-1}$)

in the same manner as in Example 4 and then, this compound was reacted with anhydrous D-(−)-α-aminobenzylpenicillin (1.75 g, 5 mM) to give D-α-(2-methyl-4-carboxyimidazole-5-carboxamido) benzylpenicillin.-monohydrate (0.6 g, yield: 23.1%) in the same manner.
M.P., 194°–200° C. (dec.)
Elemental analysis:
  Found C 50.88%, H 4.65%, N 14.02%
  Calcd. for $C_{22}H_{23}N_5SO_7 \cdot H_2O$ C 50.85%, H 4.86%, N 13.48%
TLC (silica gel) $R_f=0.61$
I.R. spectrum (Nujol):

$\nu_{C=O}(\beta\text{-lactam})=1775 \text{ cm}^{-1}$

The N.M.R. spectrum of the 2 Na salt of this compound is as follows: ($D_2O$, δ)

ppm
  1.50 (bs, 6H)

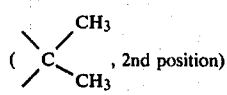

2.40 (s, 3H) (—CH₃, 2nd position in the imidazole)
4.20 (5, 1H) (—H, 3rd position)
5.40–5.80 (m, 3H)

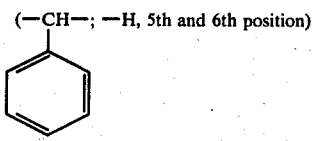

7.30 (bs, 5H)

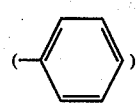

The disodium salt of this compound [V] was produced in the same manner as in Example 1.

Example 7

2-Hydroxyimidazole-4,5-dicarboxylic acid dibutyl ester (11.4 g, 0.04 M) was dissolved in phosphorus oxychloride (80 ml) and refluxed for 4 hours.

The reaction mixture was concentrated under reduced pressure and thereby phosphorus oxychloride was removed. The resulting phosphorus oxychloride was hydrolyzed by adding ice-water (200 ml) to the concentrated reaction mixture. The mixture was extracted twice with ethyl acetate (200 ml). The obtained ethyl acetate solution was dried with anhydrous sodium sulfate and concentrated under reduced pressure to give a brown colored residue. This residue was dissolved in 0.5 N NaOH solution (200 ml) and the mixture was stirred at room temperature to hydrolyze the ester. The mixture was adjusted to pH 2 with dilute hydrochloric acid solution and ethyl acetate (200 ml) was added thereto and thereby unreacted material was separated and removed.

The water solution obtained above was adjusted to pH 5.6 and concentrated under reduced pressure to yield a reside (30 ml). The precipitated crystals were obtained by filtration to give 2-chloroimidazole-4,5-dicarboxylic acid sodium salt (2.4 g, yield: 28.3%).
M.P., more than 280° C. (dec.)
Elemental analysis:
  Found C 27.93%, H 1.05%, N 13.23%
  Calcd. for C₅H₂N₂O₄Cl Na C 28.2%, H 0.94%, N 13.2%

The thus obtained 2-chloroimidazole-4,5-dicarboxylic acid sodium salt (0.76 g, 4 mM) was converted to the acid chloride derivative thereof

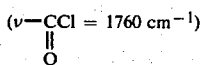

in the same manner as in Example 4, and this derivative was reacted with anhydrous D-(—)-α-aminobenzylpenicillin (0.7 g, 2 mM) to give D-α-(2-chloro-4-carbox- yimidazole-5-carboxamido)benzylpenicillin (0.59 g, yield: 57.0%) in the same manner.
M.P., 183°–190° C. (dec.)
Elemental analysis:
  Found C 48.98%, H 4.37%, N 13.36% S 5.81%, Cl 6.46%
  Calcd. for C₂₁H₂₀N₅SClO₇ C 48.32%, H 3.87%, N 13.42% S 6.14%, Cl 6.79%
TLC (silica gel) R$_f$=0.76
I.R. spectrum (Nujol):

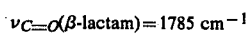

The N.M.R. spectrum of the 2 Na salt of this compound [VI] is as follows: (D₂O, δ) ppm
1.43 (bs, 6H)

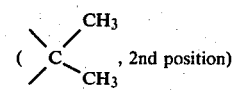

4.13 (s, 1H) (—H, 3rd position)
5.30–5.70 (m, 3H)

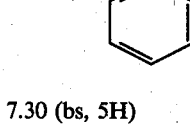

7.30 (bs, 5H)

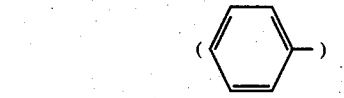

Example 8

2-Aminoimidazole-4,5-dicarboxylic acid (1.2 g, 7 mM) was suspended in dry benzene (20 ml) and HCl gas was passed through the solution for 10 minutes. To this solution DMF (3 drops) and thionyl chloride (5 ml) were added and this mixture was refluxed at 80° C. for 4.5 hours. The acid chloride derivative

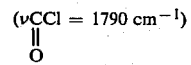

obtained in the same manner as in Example 4 was reacted with anhydrous D-(—)-α-aminobenzylpenicillin (1.75 g, 5 mM) to give D-α-(2-amino-4-carboxyimidazole-5-carboxamido)benzylpenicillin (0.3 g, yield: 12.2%).
M.P., 195°–208° C. (dec.)
Elemental analysis:
  Found C 50.68%, H 4.96%, N 17.00%
  Calcd. for C₂₁H₂₂N₆SO₇ C 50.19%, H 4.42%, N 16.73%
TLC (silica gel) R$_f$=0.69
I.R. spectrum (Nujol)

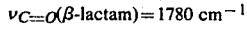

The N.M.R. spectrum of the 2 Na salt of this compound is as fofllows: (D$_2$O, δ) ppm 1.45 (bs, 6H)

( >C<CH$_3$/CH$_3$ , 2nd position)

4.13 (s, 1H) (—H, 3rd position)
5.20–5.80 (m, 3H)

(—CH—; —H, 5th and 6th position, phenyl)

7.23 (bs, 5H)

( phenyl )

The disodium salt of this compound [VII] was produced by the same method as in Example 1.

Example 9

7-β-[D-(—)-α-(4-carboxyimidazole-5-carboxyamido)phenylacetamido]cephalosporamic acid.2Na salt (770 mg, 1.3 mM) as obtained in Example 2, and 1-methyl-5-mercapto-1H-tetrazole (150 mg, 1.3 mM) were dissolved in pH 6.4 phosphate buffer solution (10 ml). At this time, the solution was adjusted to pH 6.4 with 2N NaOH solution. This solution was reacted at 60° C. with stirring for 24 hours. 5 Hours after starting the reaction, the mixture was adjusted to pH 6.4 with 2N NaOH solution.

To the reaction mixture water (20 ml) was added and the solution was adjusted to pH 7. The aqueous solution was washed with ethyl acetate (30 ml). To the obtained aqueous layer ethyl acetate (50 ml) was added and 6% hydrochloric acid solution was added to adjust the aqueous layer to pH 2. An insoluble material was removed by filtration to yield a solution having 2 layers. The aqueous solution was extracted with ethyl acetate (50 ml), once more. The obtained ethyl acetate solutions were combined, washed with water and dried with anhydrous magnesium sulfate. The ethyl acetate solution was concentrated at less than 30° C. and the residue was triturated with ether (50 ml). The triturated material was obtained by filtration and dried to give the desired compound, 7-β-[-(—)-α-(4-carboxyimidazole-5-carboxamido)phenylacetamido]-3-[[(1-methyl-1H-tetrazol-5-yl)thio]methyl]-3-cephem-4-carboxylic acid monohydrate (160 mg, yield: 27%).

The 2 Na salt of this compound [VIII] was produced in the same manner as in Example 1.
M.P., 180°–190° C. (dec.)
Elemental analysis:
 Found C 43.01%, H 3.56%, Na 6.33%
 Calcd. for C$_{23}$H$_{19}$N$_9$O$_7$S$_2$Na$_2$ C 41.81%, H 3.06%, Na 6.96%
TLC (silica gel) R$_f$=0.23

I.R. spectrum (Nujol):

$\nu_{C=O}$(β-lactam)=1765 cm$^{-1}$

N.M.R. spectrum (D$_2$O, δ) ppm
 3.10–3.60 (m, 2H) (>CH$_2$, 2nd position)
 3.88 (s, 3H) (—CH$_3$ in the tetrazole)
 4.00–4.20 (m, 2H) (—CH$_2$—S—, 3rd position)
 4.93 (d, 1H) (—H, 6th position)
 5.31–5.68 (m, 2H)

(—H, 7th position; —CH—, phenyl)

7.30 (bs, 5H)

( phenyl )

7.63 (s, 1H) (—H, 2nd position in imidazole)

Example 10

7-β-[D-(—)-α-(4-carboxyimidazole-5-carboxamido)-phenylacet-amido]cephalosporanic acid.2Na salt (1.17 g, 2 mM) as produced in the Example 2, was dissolved in water (12 ml) and 4-pyridineethanesulfonic acid (0.75 g, 4 mM) was added thereto. The solution was adjusted to pH 7 with 2N NaOH solution. To this solution potassium iodide (8.3 g) was added and this solution was reacted at 70° C. with stirring for 2 hours. The reaction mixture was treated with Amberlite XAD-2 produced by Rohm & Haas Co. (700 ml) in a column. By elution with water the fractions having the desired compound were collected. The solution was lyophilized to give the object compound, 7-β-[D-(—)-α-(4-carboxyimidazole-5-carboxamido)phenylacetamido]-3-(4-β-sulphoethyl-pyridinium)-methyl-3-cephem-4-carboxylic acid as the mixed K salt phentahydrate [IX] (0.2 g, yield: 14%).
M.P. 198°–205° C.
Elemental analysis:
 Found C 39.51%, H 3.43%, N 9.51%
 Calcd. for C$_{28}$H$_{24}$N$_6$O$_{10}$S$_2$K$_2$.5H$_2$O C40.18%, H4.10%, N 10.04%
TLC (silica gel) R$_f$=0.15
I.R. spectrum (Nujol):

$\nu_{C=O}$(β-lactam)=1765 cm$^{-1}$ $\nu_{SO_2}$(—SO$_3$H)=1190, 1040 cm$^{-1}$ N.M.R. spectrum (D$_2$O, δ)
ppm 3.00–3.20 (m, 2H) (>CH$_2$, 2nd position) 3.30 (s, 4H) (—CH$_2$CH$_2$SO$_3$H)
4.80–5.70 (m, 3H)

(—H, 6th and 7th position; —CH—, phenyl)

7.10–7.50 (m, 5H)

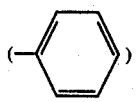

7.72 (s, 1H) (—H, 2nd position in imidazole)
7.80 (d, 2H)
8.30 (d, 2H) }

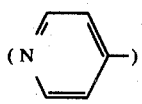

Imidazole dicarboxylic acid derivatives of the present invention have a marked antibacterial activity with wide scope, particularly against Pseudomonas aeruginosa.

Comparative MIC's for compounds using Pseudomonas aeruginosa AJ 2116 as the test organism are as follows:

| Compound No. | MIC (μg/ml) |
| --- | --- |
| I | 12.5 |
| II | 12.5 |
| III | 25 |
| IV | 50 |
| V | 50 |
| VI | 50 |
| VII | 50 |
| VIII | 50 |
| IX | 12.5 |
| Carbenicillin | 100 |
| ampicillin | More than 500 |

"MIC" represents the Minimum INhibitory concentration in mcg./ml of the compound required to inhibit the growth of the test organism described.

What is claimed is:

1. A compound having the following formula:

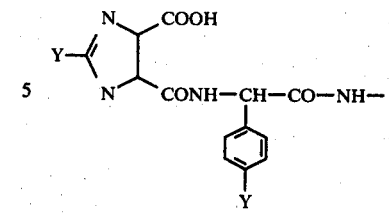

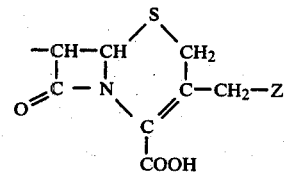

wherein
X is a group selected from the group consisting of hydrogen, halogen, hydroxy, mercapto, methyl and amino;
Y is a group selected from the group consisting of hydrogen and hydroxy; and
Z is a group selected from the group consisting of hydrogen, acetoxy, carbamoyloxy, (thiadiazolyl)thio, (methyltetrazolyl)thio, pyridinium, quinolinium, and picolinium;
and salts thereof.

2. The compound according to claim 1, wherein Z is 5-(1-methyl-tetrazolyl)thio or 2-(1, 3, 4-thiadiazolyl)thio.

3. The compound according to claim 1, wherein Z is 4-carbamoylpyridinium or 4-β-sulfoethylpyridinium.

4. The compound of claim 1 which is: 7-β-[D-(—)-α-(4-carboxyimidazole-5-carboxamido)phenylacetamido]-cephalosporanic acid and pharmaceutically acceptable salts thereof.

5. The compound of claim 1 which is: 7-β-[D-(—)-α-(4-carboxyimidazole-5-carboxamido)phenylacetamido]-3-(4-carbamoylpyridinium)methyl-3-cephem-4-carboxylic acid and pharmaceutically acceptable salts thereof.

6. The compound of claim 1 which is: 7-β-[D-(—)-α-(4-carboxyimidazole-5-carboxamido)phenylacetamido]-3-[[(1-methyl-1H-tetrazol-5-yl)thio]methyl]-3-cephem-4-carboxylic acid and pharmaceutically acceptable salts thereof.

7. The compound of claim 1 which is: 7-β-[D-(—)-α-(4-carboxyimidazole-5-carboxamido)phenylacetamido]-3-(4-β-sulphoethylpyridinium)methyl-3-cephem-4-carboxylic acid and pharmaceutically acceptable salts thereof.

* * * * *

UNITED STATES PATENT AND TRADEMARK OFFICE
CERTIFICATE OF CORRECTION

PATENT NO. : 4,217,450
DATED : August 12, 1980
INVENTOR(S) : NAOHIKO YASUDA ET AL It is certified that error appears in the above—identified patent and that said Letters Patent is hereby corrected as shown below:

First page, in the Abstract, right column, in the first formula the grouping 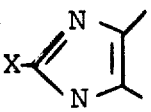

should read -- 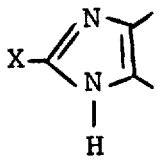 --

Column 5, lines 3 and 24, delete "7β-[D(-0-α-" and insert -- 7-β-[D-(-)-α- --.

Column 11, line 57, delete "7-β-[-(-)" and insert -- 7-β-[D-(-) --.

Column 14, first formula, the grouping

UNITED STATES PATENT AND TRADEMARK OFFICE
CERTIFICATE OF CORRECTION

PATENT NO. : 4,217,450

DATED : August 12, 1980

INVENTOR(S) : NAOHIKO YASUDA ET AL

It is certified that error appears in the above—identified patent and that said Letters Patent is hereby corrected as shown below:

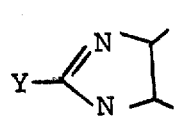   should read --   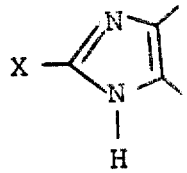   --.

Signed and Sealed this

Seventh Day of April 1981

[SEAL]

Attest:

RENE D. TEGTMEYER

Attesting Officer        Acting Commissioner of Patents and Trademarks